United States Patent
Bouchy

(10) Patent No.: US 10,183,902 B2
(45) Date of Patent: Jan. 22, 2019

(54) CATALYST COMPRISING AN IZM-2 ZEOLITE WITH AN OPTIMIZED SI/AL MOLAR RATIO, FOR THE ISOMERIZATION OF C8 AROMATIC CUTS

(71) Applicant: IFP Energies Nouvelles, Rueil-Malmaison (FR)

(72) Inventor: Christophe Bouchy, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/658,900

(22) Filed: Jul. 25, 2017

(65) Prior Publication Data
US 2018/0029957 A1   Feb. 1, 2018

(30) Foreign Application Priority Data

Jul. 26, 2016 (FR) ..................................... 16 57146

(51) Int. Cl.
| | | |
|---|---|---|
| C07C 5/27 | (2006.01) | |
| B01J 29/76 | (2006.01) | |
| B01J 29/74 | (2006.01) | |
| C10G 45/64 | (2006.01) | |

(52) U.S. Cl.
CPC ............ C07C 5/2775 (2013.01); B01J 29/74 (2013.01); B01J 29/76 (2013.01); C07C 5/2708 (2013.01); C07C 5/2737 (2013.01); C10G 45/64 (2013.01); C07C 2529/74 (2013.01)

(58) Field of Classification Search
CPC . C07C 5/2737; C07C 5/2775; C07C 2529/74; C10G 45/64; B01J 29/74; B01J 29/76
See application file for complete search history.

(56) References Cited

U.S. PATENT DOCUMENTS 8,629,073 B2   1/2014  Guillon

FOREIGN PATENT DOCUMENTS

| WO | 2010015733 A1 | 2/2010 |
| WO | 2013153317 A1 | 10/2013 |

OTHER PUBLICATIONS

Search Report dated Jan. 16, 2017 in corresponding FR 1657146.
English machine translation of WO2013153317 published Oct. 17, 2013.

*Primary Examiner* — Brian A McCaig
*Assistant Examiner* — Jason Y Chong
(74) *Attorney, Agent, or Firm* — Millen, White, Zelano and Branigan, P.C.

(57) ABSTRACT

A catalyst is described comprising at least one IZM-2 zeolite containing silicon atoms and aluminum atoms, at least one matrix and at least one metal from group VIII of the periodic classification of the elements, the zeolite having a ratio between the number of moles of silicon and the number of moles of aluminum in the range 60 to 150. Said catalyst is used in a process for the isomerization of an aromatic feed comprising at least one compound containing eight carbon atoms per molecule.

14 Claims, No Drawings

CATALYST COMPRISING AN IZM-2 ZEOLITE WITH AN OPTIMIZED SI/AL MOLAR RATIO, FOR THE ISOMERIZATION OF C8 AROMATIC CUTS

The present invention relates to a catalyst comprising a zeolite designated by the term IZM-2 with an optimized molar ratio of silicon to aluminium (Si/Al ratio, expressed in moles of silicon per mole of aluminium). The present invention also relates to a process for the isomerization of a $C_8$ aromatics cut using said isomerization catalyst.

PRIOR ART

Sources of aromatics containing eight carbon atoms are principally obtained from a reforming process (reformate) and from a steam cracking process (pyrolysis gasolines). The distribution of the aromatics containing eight carbon atoms in these cuts can vary: in general, 10% to 30% of ethylbenzene with a complement of the three xylene isomers: para-xylene, meta-xylene and ortho-xylene. Typically, the distribution in this xylenes complement is 50% of meta-xylene, 25% of ortho-xylene and 25% of para-xylene. Within this complement of xylenes, para-xylene is a particularly sought-after isomer. In fact, via dimethylterephthalate and terephthalic acid, this latter can be used for the production of polyester fibres used for clothing and resins and films of polyethylene terephthalate (PET). Thus, it is desirable to maximize the production of para-xylene to the detriment of the other aromatics containing eight carbon atoms. This is accomplished using catalytic isomerization processes. After extracting para-xylene, the residual cut, which is rich in meta-xylene, ortho-xylene and ethylbenzene, is sent to a catalytic isomerization unit which returns a mixture of aromatics containing eight carbon atoms in which the proportion of xylenes is close to thermodynamic equilibrium and the quantity of ethylbenzene is reduced because of the conversion of the ethylbenzene. This mixture is sent once more to a para-xylene extraction unit and the residual cut is sent to the isomerization unit. Thus, a "$C_8$ aromatics loop" is generated which can be used to maximize the production of para-xylene (E. Guillon, P. Leflaive, Techniques de l'Ingénieur [Engineering Techniques], J5920, V3). It is possible to use an isomerization unit to isomerize the xylenes into para-xylene and convert the ethylbenzene into benzene by an ethylbenzene dealkylation reaction. In this case, the term "dealkylating" isomerization of the cut is used. The residual cut may also be sent to a catalytic isomerization unit in order to isomerize the xylenes into para-xylene and convert the ethylbenzene into xylenes by an ethylbenzene isomerization reaction. This is then said to be "isomerizing" isomerization of the cut. These industrial processes generally use heterogeneous catalysts employed in fixed bed mode and operating in the vapour phase under hydrogen pressure. These two types of processes are distinguished by the operating conditions and by the formulation of the catalysts used (by their nature and/or their hydrodehydrogenating and/or acidic function content). The present invention falls within the field of "isomerizing" isomerization.

In the case of "isomerizing" isomerization, the catalyst is bifunctional in type and has both an acidic function (generally provided by at least one zeolite) and a hydrodehydrogenating function supplied by a noble metal (generally platinum). It has in fact been demonstrated that the isomerization of ethylbenzene into xylenes involves a bifunctional type mechanism. The ethylbenzene is initially hydrogenated into ethylcyclohexenes at the metallic sites, these cyclo-olefinic intermediates then being isomerized into dimethylcyclohexenes at the Brønsted acid sites. Finally, the dimethylcyclohexenes are dehydrogenated into xylenes at the metallic sites. The use of a strong hydrodehydrogenating function such as platinum also induces the production of naphthene rings by hydrogenation of the corresponding aromatic rings.

In addition to the desired isomerization reactions, it is desirable to limit the side reactions of the following type:
- dealkylation of ethylbenzene into benzene and ethylene;
- disproportionation of ethylbenzene into diethylbenzene and benzene, or of xylenes into toluene and aromatics containing 9 carbon atoms;
- transfer of alkyls between ethylbenzene and the xylenes; and between the xylenes themselves;
- naphthene ring opening and cracking.

This set of reactions cause the production of molecules which are harder to upgrade, which are not recycled to the "$C_8$ aromatics loop" and which are considered to be net losses for the process. All molecules apart from the cyclic molecules containing eight carbon atoms are therefore considered to be net losses.

The isomerization reactions as well as the side reactions are principally catalysed by the acidic function. The properties of the zeolite (number and strength of the acidic Brønsted sites, topology of microporous framework, etc) serving as the acidic function thus have a direct impact on the properties of the bifunctional catalyst, and in particular on its selectivity.

Catalysis of the isomerization of a $C_8$ aromatics cut into xylenes has been the focus of many patents pertaining to various zeolites. ZSM-5 is among the zeolites used for the isomerization of a $C_8$ aromatics cut, used alone or as a mixture with other zeolites such as mordenite, for example. These catalysts have been described in particular in the patents U.S. Pat. No. 4,467,129 B and U.S. Pat. No. 4,482,773 B. Other catalysts principally based on mordenite have been described in the patent FR 2 477 903 B, for example. A catalyst based on a zeolite with structure type EUO has also been proposed (EP 923 987), or based on a zeolite with structure type MTW (WO 2005 065380 A, WO 2010 000652 A, US 2014 0296601 A) or in fact based on a UZM-8 zeolite in the patent U.S. Pat. No. 7,091,190 B.

These examples illustrate the continued research being carried out to develop ever more powerful catalysts for the isomerization of $C_8$ aromatics cuts, in particular by minimizing the production of net losses by using appropriate zeolites. For a given zeolite structure, two factors are known to have an impact on its selectivity and thus on the selectivity of the catalyst. The first factor is the density of the Brønsted acid sites: the activity per acidic site for bimolecular reactions such as the disproportionation of ethylbenzene is proportional to the density of the acidic sites (M. Guisnet, Techniques de l'Ingënieur, j1217). From this point of view, it would thus be desirable to use a zeolite with a low site density in order to minimize the disproportionation and transalkylation side reactions. The second factor is the strength of the acidic sites: the ethylbenzene dealkylation reaction of ethylbenzene to form benzene involves the formation of unstable ethylcarbenium ions with a high energy barrier (P. Moreau, thesis, University of Poitiers, 2005) and necessitates the presence of strong acidic sites. This reaction is therefore highly sensitive to the strength of the acidic sites of the zeolite. From this point of view, it is thus desirable to use a zeolite having few strong acidic sites in order to minimize this type of side reaction. However, for a given zeolitic structure, the strength of the acidic sites is a function of their density: the acidic sites are much stronger as they become more isolated, and thus their density is low (C. Marcilly, catalyse acido-basique [Acido-basic catalysis], volume 1, 2003). From this point of view, it would thus be desirable to use a zeolite with a high site density in order to minimize dealkylation side reactions. Minimizing the various side reactions thus makes contradictory demands in terms of the density of the acidic sites. In addition, and finally, the density of the acidic sites and their force also dictate the overall activity of the zeolite.

To this end, for a given zeolitic structure, it is necessary to identify the optimal range for the density of the acidic sites in order to obtain the best compromise between activity and selectivity. The density of the acidic sites of a zeolite is also a function of the ratio between the number of moles of silicon and the number of moles of aluminium in said zeolite.

Recently, the Applicant's research has led to the development of a novel zeolite, IZM-2 zeolite (FR 2 918 050 B) which is hereby incorporated into the present application by reference, and also its use in a catalyst for the isomerization of a cut containing at least one aromatic compound containing eight carbon atoms (FR 2 934 793 B). FR 2 918 050 B discloses a solid IZM-2 with a molar ratio in the range 1 to 500. In the illustrative example of patent FR 2 934 793 B, only a solid IZM-2 with a molar ratio Si/Al of 53 is used for the isomerization of a cut containing at least one aromatic compound containing eight carbon atoms.

In addition, one aim of the present invention is to provide a novel catalyst for the isomerization of a $C_8$ aromatics cut comprising an IZM-2 zeolite with an optimized Si/Al molar ratio, which has an X ray diffraction diagram as given below, in order to limit the production of net losses.

SUMMARY OF THE INVENTION

The present invention concerns a catalyst comprising at least one IZM-2 zeolite, at least one matrix and at least one metal from group VIII of the periodic classification of the elements, said catalyst being characterized in that the ratio between the number of moles of silicon and the number of moles of aluminium of the IZM-2 zeolite is in the range 60 to 150.

In the context of the present invention, the term "ratio between the number of moles of silicon and the number of moles of aluminium of the IZM-2 zeolite" means the ratio of the number of moles of silicon divided by the number of moles of aluminium of the framework of the IZM-2 zeolite.

The catalyst in accordance with the invention is advantageously used in a process for the isomerization of an aromatic cut comprising at least one aromatic compound containing eight carbon atoms per molecule, using the following operating conditions:
  a temperature of 300° C. to 500° C.,
  a partial pressure of hydrogen of 0.3 to 1.5 MPa,
  a total pressure of 0.45 to 1.9 MPa, and
  a supply space velocity, expressed in kilograms of feed introduced per kilogram of catalyst and per hour, of 0.25 to 30 $h^{-1}$.

It has surprisingly been discovered that the catalyst in accordance with the invention comprising at least one matrix, at least one metal from group VIII of the periodic classification of the elements, and at least one IZM-2 zeolite in accordance with the invention wherein the molar ratio Si/Al is in the range 60 to 110, preferably in the range 60 to 100, highly preferably in the range 60 to 95, more preferably in the range 60 to 80 and yet more preferably in the range 60 to 70, results in improved catalytic performances in terms of selectivity during a process for the isomerization of an aromatic feed containing at least one aromatic cut comprising at least one aromatic compound containing eight carbon atoms per molecule. A catalyst of this type is substantially more selective than a catalyst comprising an IZM-2 zeolite with a Si/Al molar ratio which is less than 60. This then results in a reduction in the production of net losses in order to obtain a given yield in para-xylene when the isomerization process is carried out in the presence of the catalyst in accordance with the invention.

DETAILED DESCRIPTION OF THE INVENTION

The present invention concerns a catalyst comprising and preferably constituted by at least one IZM-2 zeolite containing silicon atoms and aluminium atoms, at least one matrix and at least one metal from group VIII of the periodic classification of the elements, said catalyst being characterized in that the ratio between the number of moles of silicon and the number of moles of aluminium of the IZM-2 zeolite is in the range 60 to 150.

Advantageously, the catalyst in accordance with the invention is characterized in that it comprises an IZM-2 zeolite wherein the ratio of the number of moles of silicon divided by the number of moles of aluminium of the zeolite framework is in the range 60 to 110, preferably in the range 60 to 100, more preferably in the range 60 to 95, yet more preferably in the range 60 to 80 and highly preferably in the range 60 to 70.

IZM-2 Zeolite

In accordance with the invention, the catalyst comprises IZM-2 zeolite. The IZM-2 zeolite has an X ray diffraction diagram including at least the peaks recorded in Table 1. IZM-2 has a crystalline structure.

Advantageously, the diffraction diagram is obtained by radiocrystallographic analysis using a diffractometer and employing the conventional powder technique with the $K_{\alpha 1}$ peak of copper ($\lambda$=1.5406 Å). From the position of the diffraction peaks represented by the angle 2θ, the characteristic interplanar spacings $d_{hkl}$ of the sample are calculated using the Bragg relationship. The error in the measurement $\Delta(d_{hkl})$ of $d_{hkl}$ is calculated by the Bragg relationship as a function of the absolute error $\Delta(2\theta)$ in the measurement of 2θ. An absolute error $\Delta(2\theta)$ of ±0.02° is customarily acceptable. The relative intensity $I_{rel}$ in each value of $d_{hkl}$ is measured from the height of the corresponding diffraction line. The X ray diffraction diagram of the IZM-2 zeolite of the invention comprises at least the peaks at the values of $d_{hkl}$ given in Table 1. In the $d_{hkl}$ column, the mean values of the interplanar spacings are shown in Angstroms (Å). Each of these values must be supplemented with an error measurement $\Delta(d_{hkl})$ in the range ±0.6 Å to ±0.01 Å.

TABLE 1

Mean values of $d_{hkl}$ and relative intensities measured on an X ray diffraction diagram of the calcined IZM-2 zeolite

| 2 theta (°) | $d_{hkl}$ (Å) | $I_{rel}$ |
|---|---|---|
| 5.07 | 17.43 | Vw |
| 7.36 | 12.01 | Vs |
| 7.67 | 11.52 | Vs |
| 8.78 | 10.07 | S |
| 10.02 | 8.82 | Vw |

TABLE 1-continued

Mean values of $d_{hkl}$ and relative intensities measured on an X ray diffraction diagram of the calcined IZM-2 zeolite

| 2 theta (°) | $d_{hkl}$ (Å) | $I_{rel}$ |
|---|---|---|
| 12.13 | 7.29 | Vw |
| 14.76 | 6.00 | Vw |
| 15.31 | 5.78 | Vw |
| 15.62 | 5.67 | Vw |
| 16.03 | 5.52 | Vw |
| 17.60 | 5.03 | Vw |
| 18.22 | 4.87 | Vw |
| 19.01 | 4.66 | Vw |
| 19.52 | 4.54 | Vw |
| 21.29 | 4.17 | M |
| 22.44 | 3.96 | W |
| 23.10 | 3.85 | Mw |
| 23.57 | 3.77 | W |
| 24.65 | 3.61 | Vw |
| 26.78 | 3.33 | W |
| 29.33 | 3.04 | Vw |
| 33.06 | 2.71 | Vw |
| 36.82 | 2.44 | Vw |
| 44.54 | 2.03 | Vw | in which:
Vs = very strong;
S = strong;
M = medium;
Mw = medium weak;
W = weak;
Vw = very weak The relative intensity $I_{rel}$ is given as a ratio with respect to a relative intensity scale where a value of 100 is attributed to the most intense peak in the X ray diffraction diagram: Vw<15; 15≤W<30; 30≤Mw<50; 50≤M<65; 65≤S<85; Vs≥85.

IZM-2 has a chemical composition, expressed on the anhydrous basis, in terms of the moles of oxides, which is defined by the following general formula: $SiO_2$: a $Al_2O_3$: b $M_{2/n}O$, in which M is at least one alkali metal and/or alkaline earth metal with valency n. In said formula given above, a represents the number of moles of $Al_2O_3$ and between represents the number of moles of $M_{2/n}O$.

In accordance with the invention, the number of moles of aluminium of the framework per gram of IZM-2 zeolite is determined from the percentage (%) by weight (by wt) of aluminium of the zeolite and from the percentage of tetracoordinated and pentacoordinated aluminium present in the zeolite in accordance with the formula:

$$n_{Al} = [(\% \text{ by wt Al}) * (\% \text{ NMRAl}^{IV} + \% \text{ NMRAl}^{V})] / [MM(Al) * 10000]$$

in which $n_{Al}$: moles of aluminium in the framework per gram of zeolite, in mole/gram, % by wt Al: percentage by weight of aluminium in the zeolite (dry mass), measured by inductively coupled plasma (ICP) on a SPECTRO ARCOS ICP-OES instrument from SPECTRO in accordance with the ASTM method D7260, MM(Al): molar mass of aluminium, in gram/mole, % NMRAl$^{IV}$: percentage by weight of tetracoordinated aluminium in the zeolite, measured by $^{27}$Al nuclear magnetic resonance, % NMRAl$^{V}$: percentage by weight of pentacoordinated aluminium in the zeolite, measured by $^{27}$Al nuclear magnetic resonance.

The percentage by weight of tetracoordinated and pentacoordinated aluminium atoms present in the IZM-2 zeolite is determined by solid $^{27}$Al nuclear magnetic resonance. Aluminium NMR is in fact known for its use in characterizing and quantifying the various coordination states of this nucleus ("Analyse physico-chimiques des catalysts industriels" [Physico-chemical analyses of industrial catalysts], J Lynch, Technip (2001), Chapter 13, pages 290 and 291). The aluminium NMR spectrum of IZM-2 zeolite exhibits three signals, a first being characteristic of the resonance of tetracoordinated aluminium atoms, a second being characteristic of pentacoordinated aluminium atoms, and a third being characteristic of the resonance of tetracoordinated aluminium atoms. Tetracoordinated aluminium atoms (denoted Al$^{IV}$) resonate at a chemical displacement which is typically in the range +50 ppm to +70 ppm, pentacoordinated aluminium atoms (denoted Al$^{V}$) resonate at a chemical displacement which is typically in the range +20 ppm to +40 ppm, and hexacoordinated aluminium atoms (denoted Al$^{VI}$) typically resonate at a chemical displacement in the range −20 ppm to +10 ppm. The percentage by weight of the various aluminium species is quantified by integrating the signals corresponding to each of these species. More precisely, the IZM-2 zeolite present in the catalyst of the invention was analysed by solid $^{27}$Al MAS-NMR on an Avance type Brücker spectrometer, 400 MHz, using a 4 mm probe optimized for $^{27}$Al. The rate of rotation of the sample was close to 14 kHz. The aluminium atom is a quadripolar nucleus with a spin of 5/2. Under "selective" analysis conditions, namely a low radiofrequency field of 30 kHz, a low pulse angle of π/2 and in the presence of a water-saturated sample, the magic angle spinning (MAS) NMR technique, denoted MAS-NMR, is a quantitative technique. Decomposition of each MAS-NMR spectrum provides direct access to the quantity of the various aluminium species, namely the tetracoordinated aluminium atoms Al$^{IV}$, the pentacoordinated Al$^{V}$ and the hexacoordinated aluminium atoms Al$^{VI}$. Each spectrum is characterized by the chemical displacement with respect to a molar aluminium nitrate solution which has an aluminium signal at zero ppm. The signals characterizing the tetracoordinated aluminium atoms Al$^{IV}$ are typically integrated between +50 ppm and +70 ppm, which corresponds to area 1, the signals characterizing the pentacoordinated aluminium atoms Al$^{V}$ are typically integrated between +20 ppm and +40 ppm, which corresponds to area 2, and the signals characterizing the hexacoordinated aluminium atoms Al$^{VI}$ are typically integrated between −20 ppm and +10 ppm, which corresponds to area 3. The percentage by weight of each aluminium species is calculated from the ratio between its area and the total area. As an example, the percentage by weight of hexacoordinated aluminium atoms Al$^{VI}$ (denoted % NMRAl$^{VI}$) is calculated as follows:

$$\% \text{ NMRAl}^{VI} = (\text{area 3}) * 100 / (\text{area 1} + \text{area 2} + \text{area 3})$$

Advantageously, the IZM-2 zeolite in accordance with the invention has a percentage by weight of hexacoordinated aluminium atoms Al$^{VI}$ (denoted % NMRAl$^{VI}$) of less than 50%, preferably less than 40%, and more preferably less than 30%.

The number of moles of silicon per gram of IZM-2 zeolite is determined from the percentage (%) by weight (by wt) of silicon of the zeolite in accordance with the formula:

$$n_{Si} = [(\% \text{ by wt Si}) / [MM(Si) * 100]$$

in which $n_{Si}$: moles of silicon per gram of zeolite, in mole/gram,

% by wt Si: percentage by weight of aluminium in the zeolite (dry mass), measured by X ray fluorescence with fused glass sample disks on an AXIOS instrument from PANalytical operating at 125 mA and 32 kV, MM(Si): molar mass of silicon, in gram/mole.

The ratio of the number of moles of silicon divided by the number of moles of aluminium of the IZM-2 zeolite framework (Si/Al) is calculated in accordance with the formula:

$$Si/Al = n_{Si}/n_{Al}$$

in which $n_{Si}/n_{Al}$: ratio of the number of moles of silicon divided by the number of moles of framework aluminium, in mole/mole, $n_{Si}$: moles of silicon per gram of zeolite, in mole/gram, $n_{Al}$: moles of aluminium of the framework per gram of zeolite, in mole/gram.

The IZM-2 zeolite comprised in the catalyst in accordance with the invention has a molar ratio Si/Al in the range 60 to 110, preferably in the range 60 to 100, more preferably in the range 60 to 95, yet more preferably in the range 60 to 80 and highly preferably in the range 60 to 70.

In accordance with the invention, the molar ratio Si/Al desired for the IZM-2 zeolite may be obtained directly during the step for synthesis of the zeolite by adjusting the synthesis conditions and in particular the composition of the synthesis gel by controlling, for example, the relative quantities of silicon and aluminium engaged in the synthesis gel.

A process for the preparation of IZM-2 zeolite is disclosed in the patent FR 2 918 050 B which is hereby incorporated by reference.

Advantageously, an aqueous mixture comprising at least one source of at least one oxide $SiO_2$, optionally at least one source of at least one oxide $Al_2O_3$, optionally at least one source of at least one alkali metal and/or alkaline-earth metal with valency n, and preferably at least one organic species R comprising two quaternary nitrogen atoms is reacted, the mixture preferably having the following molar composition:

$SiO_2/Al_2O_3$: at least 2, preferably at least 20, yet more preferably 60 to 600, $H_2O/SiO_2$: 1 to 100, preferably 10 to 70, $R/SiO_2$: 0.02 to 2, preferably 0.05 to 0.5, $M_{2/n}O/SiO_2$: 0 to 1, preferably 0.005 to 0.5, where M is one or more alkali and/or alkaline-earth metal(s) selected from lithium, sodium, potassium, calcium, magnesium and a mixture of at least two of these metals; preferably, M is sodium. Advantageously, the element R is 1,6-bis(methylpiperidinium)hexane.

In accordance with the invention, the molar ratio Si/Al of the IZM-2 zeolite may also be adjusted to the desired value by methods for the post-treatment of the IZM-2 zeolite obtained after synthesis. Such methods are known to the person skilled in the art and can be used to carry out dealumination or desilication of the zeolite. Preferably, the Si/Al molar ratio of the IZM-2 zeolite forming part of the composition of the catalyst in accordance with the invention is adjusted by an appropriate choice of the conditions for synthesizing said zeolite.

The IZM-2 zeolite present in the catalyst in accordance with the invention is highly advantageously in its acidic form, i.e. in the protonated form, $H^+$. In such a case, it is advantageous for the ratio of the number of moles of cation other than the proton per gram of IZM-2 zeolite divided by the number of moles of aluminium of the framework per gram of IZM-2 zeolite to be less than 0.9, preferably less than 0.6 and highly preferably less than 0.3. To this end, the IZM-2 zeolite forming part of the composition of the catalyst in accordance with the invention may, for example, be exchanged by means of at least one treatment using a solution of at least one ammonium salt in a manner such as to obtain the ammonium form of the IZM-2 zeolite which, once calcined, produces the acidic form of said IZM-2 zeolite. This exchange step may be carried out at any stage of the preparation of the catalyst, i.e. after the step for preparation of the IZM-2 zeolite, after the step for shaping the IZM-2 zeolite with a matrix, or indeed after the step for introducing the hydrodehydrogenating metal. Preferably, the exchange step is carried out after the step for shaping the IZM-2 zeolite.

Matrix

In accordance with the invention, the catalyst comprises at least one matrix. Said matrix may advantageously be amorphous or crystalline.

Preferably, said matrix is advantageously selected from the group formed by alumina, silica, silica-alumina, clays, titanium oxide, boron oxide and zirconia, used alone or as a mixture, or it may also be selected from the aluminates. Preferably, alumina is used as the matrix. Preferably, said matrix contains alumina in any of its forms known to the person skilled in the art such as, for example, alpha, gamma, eta or delta type aluminas. Said aluminas differ in their specific surface area and their pore volume. The mixture of the matrix and the shaped IZM-2 zeolite constitutes the catalyst support.

Metallic Phase

In accordance with the invention, the catalyst comprises at least one metal from group VIII preferably selected from iron, cobalt, nickel, ruthenium, rhodium, palladium, osmium, iridium and platinum, preferably selected from noble metals from group VIII, more preferably selected from the palladium and platinum, and highly preferably, platinum is selected.

The dispersion of the metal(s) from group VIII, determined by chemisorption, for example by $H_2/O_2$ titration or by carbon monoxide chemisorption, is in the range 10% to 100%, preferably in the range 20% to 100% and highly preferably in the range 30% to 100%. The macroscopic distribution coefficient of the metal(s) from group VIII, obtained from its (their) profile determined using a Castaing microprobe, defined as the ratio of the concentrations of the metal(s) from group VIII in the core of the grain with respect to the edge of that grain, is in the range 0.7 to 1.3, preferably in the range 0.8 to 1.2. The value for this ratio, close to 1, is evidence of the homogeneity of the distribution of the metal(s) from group VIII in the catalyst.

Said catalyst may advantageously comprise at least one additional metal selected from the group formed by metals from groups IIIA, IVA and VIIB of the periodic classification of the elements, and preferably selected from gallium, indium, tin and rhenium. Said additional metal is preferably selected from indium, tin and rhenium.

Preparation of Catalyst

The catalyst in accordance with the invention may advantageously be prepared in accordance with any of the methods which are well known to the person skilled in the art.

Shaping

Advantageously, the various constituents of the support or catalyst may be shaped by a step for milling in order to form a paste, then extrusion of the paste obtained, or in fact by mixing the powders then pelletization, or in fact using any other known process for agglomerating a powder containing alumina. The supports obtained in this manner may have various shapes and dimensions. Preferably, shaping is carried out by milling and extrusion.

During shaping of the support by milling then extrusion, said IZM-2 zeolite may be introduced while dissolving or suspending the compounds of alumina or alumina precursors such as boehmite, for example. Although this is not limiting, said IZM-2 zeolite may, for example, be in the form of a powder, ground powder, suspension, or suspension which has undergone deagglomeration. Thus, for example, said zeolite may advantageously be placed in acidified suspension or otherwise at a concentration which is adjusted to the final content of IZM-2 envisaged for the catalyst in accordance with the invention. This suspension, which is generally known as a slip, is then mixed with the alumina compounds or the alumina precursors.

Furthermore, additives may advantageously be employed in order to facilitate shaping and/or to improve the final mechanical properties of the supports, as is well known to the person skilled in the art. Examples of additives which may in particular be cited are cellulose, carboxymethyl cellulose, carboxyethyl cellulose, tall oil, xanthan gums, surfactants, flocculating agents such as polyacrylamides, carbon black, starches, stearic acid, polyacrylic alcohol, polyvinyl alcohol, biopolymers, glucose, polyethylene glycols, etc.

Advantageously, water may be added or removed in order to adjust the viscosity of the paste to be extruded. This step may advantageously be carried out at any stage of the milling step.

In order to adjust the solid matter content of the paste to be extruded in order to make it possible to extrude, it is also possible to add a compound which is primarily solid and preferably an oxide or a hydrate. Preferably, a hydrate is used, more preferably an aluminium hydrate. The loss on ignition of this hydrate is advantageously more than 15%.

Extrusion of the paste obtained from the milling step may advantageously be carried out using any conventional tool which is commercially available. The paste obtained from milling is advantageously extruded through a die, for example with the aid of a piston or a single or double extrusion screw. The extrusion may advantageously be carried out using any method known to the person skilled in the art.

The supports for the catalysts in accordance with the invention are generally in the form of cylindrical or polylobed extrudates such as bilobes, trilobes, polylobes, with a straight or twisted shape, but may optionally be produced and used in the form of crushed powders, tablets, rings, beads and/or wheels. Preferably, the catalyst supports in accordance with the invention are in the shape of spheres or extrudates. Advantageously, the support is in the form of extrudates with a diameter in the range 0.5 to 5 mm, and more particularly in the range 0.7 to 2.5 mm. The shapes may be cylindrical (which may or may not be hollow) and/or twisted cylinders and/or multilobes (2, 3, 4 or 5 lobes for example), and/or rings. The multilobed shape is preferred and advantageous for use.

Drying

The support thus obtained may then undergo a drying step. Said drying step is advantageously carried out using any technique known to the person skilled in the art.

Preferably, drying is carried out in a stream of air. Said drying may also be carried out in a stream of any oxidizing, reducing or inert gas. Preferably, drying is advantageously carried out at a temperature in the range 50° C. to 180° C., preferably in the range 60° C. to 150° C. and more preferably in the range 80° C. to 130° C.

Calcining

Said support, optionally dried, then preferably undergoes a calcining step.

Said calcining step is advantageously carried out in the presence of molecular oxygen, for example by flushing with air, at a temperature which is advantageously more than 200° C. and less than or equal to 1100° C. Said calcining step may advantageously be carried out in a flushed bed, a trickle bed or in a static atmosphere. As an example, the furnace used may be a rotary furnace or a vertical furnace with radial flushed beds. Preferably, said calcining step is carried out for between more than one hour at 200° C. to less than one hour at 1100° C. Calcining may advantageously be carried out in the presence of steam and/or in the presence of an acidic or basic vapour. As an example, calcining may be carried out under a partial pressure of ammonia.

Post-Calcining Treatments

Post-calcining treatments may optionally be carried out in a manner such as to improve the properties of the support, in particular the textural properties.

Thus, the catalyst support used in the process in accordance with the present invention may undergo a hydrothermal treatment in a confined atmosphere. The term "hydrothermal treatment in a confined atmosphere" means a treatment by passage through an autoclave in the presence of water at a temperature above ambient temperature, preferably above 25° C. and more preferably above 30° C.

During this hydrothermal treatment, the support may advantageously be impregnated, prior to passage through the autoclave (autoclaving being carried out either in the vapour phase or in the liquid phase, this vapour or liquid phase of the autoclave possibly being acidic or otherwise). This impregnation prior to autoclaving may advantageously be acidic or otherwise. This impregnation prior to autoclaving may advantageously be carried out dry or by immersing the support in an aqueous acidic solution. The term "dry impregnation" means bringing the support into contact with a volume of solution which is less than or equal to the total pore volume of the support. Preferably, the impregnation is carried out dry. The autoclave is preferably a rotating basket autoclave such as that defined in the patent application EP 0 387 109 A. The temperature during autoclaving may be in the range 100° C. to 250° C. for a period in the range 30 minutes to 3 hours.

Deposition of Metallic Phase

In order to deposit the metal from group VIII of the periodic classification of the elements, any of the techniques for depositing which are known to the person skilled in the art and any precursors of such metals may be suitable. It is possible to use techniques for deposition by dry impregnation or by excess impregnation of a solution containing precursors of the metals, in the presence or absence of competing agents. The metal may be introduced at any step of the preparation of the catalyst: onto the IZM-2 zeolite and/or onto the matrix, in particular before the shaping step, during the shaping step or after the shaping step, onto the catalyst support. Preferably, the metal is deposited after the shaping step.

Controlling certain parameters employed during deposition, in particular the nature of the precursor of the metal(s) from group VIII used, means that deposition of said metal(s) can be orientated primarily onto the matrix or onto the zeolite.

Thus, in order to introduce the metal(s) from group VIII, preferably platinum and/or palladium, primarily onto the matrix, it is possible to use an anionic exchange with hexachloroplatinic acid and/or hexachloropalladic acid, in the presence of a competing agent, for example hydrochloric acid, deposition generally being followed by calcining, for example at a temperature in the range 350° C. to 550° C. and for a period in the range 1 to 4 hours. Using precursors of this type, the metal(s) from group VIII is(are) deposited primarily on the matrix and said metal(s) has (have) good dispersion and good macroscopic distribution through the catalyst grain.

It is also possible to envisage depositing the metal(s) from group VIII, preferably platinum and/or palladium, by cationic exchange so that said metal(s) are deposited mainly on the zeolite. Thus, in the case of platinum, the precursor may, for example, be selected from:

ammoniacal compounds such as salts of platinum (II) tetramines with formula $Pt(NH_3)_4X_2$, salts of platinum (IV) hexamines with formula $Pt(NH_3)_6X_4$; salts of platinum (IV) halogenopentamines with formula $(PtX(NH_3)_5)X_3$; salts of platinum N-tetrahalogenodiamines with formula $PtX_4(NH_3)_2$; and halogenated compounds with formula $H(Pt(acac)_2X)$;

X being a halogen selected from the group formed by chlorine, fluorine, bromine and iodine, X preferably being chlorine, and "acac" representing the group acetylacetonate (with empirical formula $C_5H_7O_2$), derived from acetylacetone. With precursors of this type, the metal(s) from group VIII is(are) deposited primarily on the zeolite and said metal(s) has(have) good dispersion and good macroscopic distribution through the catalyst grain.

In the case in which the catalyst of the invention also contains at least one metal selected from metals from groups IIIA, IVA and VIIB, any of the techniques for depositing a metal of this type known to the person skilled in the art and any of the precursors of such metals may be suitable.

It is possible to add the metal(s) from group VIII and that(those) from groups IIIA, IVA and VIIB either separately or simultaneously in at least one single step. When at least one metal from groups IIIA, IVA and VIIB is added separately, it is preferably added after the metal from group VIII.

The additional metal selected from the metals from groups IIIA, IVA and VIIB may be introduced via compounds such as, for example, the chlorides, bromides and nitrates of metals from groups IIIA, IVA and VIIB. As an example, in the case of indium, the nitrate or chloride is used, and in the case of rhenium, perrhenic acid is advantageously used. The additional metal selected from the metals from groups IIIA, IVA and VIIB may also be introduced in the form of at least one organic compound selected from the group constituted by complexes of said metal, in particular polyketone complexes of the metal and hydrocarbyl metals such as metal alkyls, cycloalkyls, aryls, alkylaryls and arylalkyls. In this latter case, the metal is advantageously introduced with the aid of a solution of an organometallic compound of said metal in an organic solvent. It is also possible to employ organohalogen compounds of the metal. Particular examples of organic compounds of metals which may be cited are tetrabutyltin, in the case of tin, and triphenylindium, in the case of indium.

If the additional metal selected from the metals from groups IIIA, IVA and VIIB is introduced before the metal from group VIII, the compound of the metal IIIA, IVA and/or VIIB used is generally selected from the group constituted by the halide, the nitrate, the acetate, the tartrate, the carbonate and the oxalate of the metal. Thus, an aqueous solution is advantageously used for introduction. However, it may also be introduced with the aid of a solution of an organometallic compound of the metal, for example tetrabutyltin. In this case, before introducing at least one metal from group VIII, calcining in air is carried out.

In addition, intermediate treatments such as calcining and/or reduction, for example, may be carried out between the successive deposits of the various metals.

Before using it in the process in accordance with the invention, the catalyst is preferably reduced. This reduction step is advantageously carried out by a treatment in hydrogen at a temperature in the range 150° C. to 650° C. and at a total pressure in the range 0.1 to 25 MPa. As an example, a reduction consists of a constant temperature stage at 150° C. for two hours then raising the temperature to 450° C. at a rate of 1° C./min, then a constant temperature stage at 450° C. for 2 hours; during the whole of this reduction step, the flow rate of hydrogen is 1000 normal $m^3$ of hydrogen per tonne of catalyst and the total pressure is kept constant at 0.2 MPa. Any ex situ reduction method may advantageously be envisaged. A prior ex situ reduction of the final catalyst, in a stream of hydrogen, may be carried out, for example at a temperature of 450° C. to 600° C., for a period of 0.5 to 4 hours.

Said catalyst also advantageously comprises sulphur. In the case in which the catalyst of the invention contains sulphur, this may be introduced at any step of the catalyst preparation: before or after the shaping step, and/or drying and/or calcining, before and/or after introducing the metal or metals cited above, or indeed by in situ or ex situ sulphurization before the catalytic reaction. In the case of in situ sulphurization, the reduction, if the catalyst has not already been reduced, is carried out before the sulphurization. In the case of ex situ sulphurization, reduction followed by sulphurization is also carried out. Sulphurization is preferably carried out in the presence of hydrogen using any sulphurization agent which is well known to the person skilled in the art such as, for example, with dimethyl sulphide or hydrogen sulphide.

The catalysts in accordance with the invention are in a variety of shapes and dimensions. They are generally used in the form of cylindrical or polylobed extrudates such as bilobes, trilobes, polylobes with a straight or twisted shape, but may optionally be produced and used in the form of crushed powders, tablets, rings, beads and/or wheels. Preferably, the catalyst supports in accordance with the invention are in the shape of spheres or extrudates. Advantageously, the catalyst support is in the form of extrudates with a diameter in the range 0.5 to 5 mm, more particularly in the range 0.7 to 2.5 mm. The shapes may be cylindrical (which may or may not be hollow) and/or twisted cylinders and/or multilobes (2, 3, 4 or 5 lobes for example), and/or rings. The multilobed shape is preferred and advantageous for use. The deposition of the metal does not change the shape of the support.

Said catalyst in accordance with the invention more particularly comprises and is preferably constituted by:
1% to 90%, preferably 3% to 80%, and more preferably 4% to 60% by weight of the IZM-2 zeolite in accordance with the invention,
0.01% to 4%, preferably 0.05% to 2% by weight of at least one metal from group VIII of the periodic classification of the elements, preferably platinum,
optionally 0.01% to 2%, preferably 0.05% to 1% by weight of at least one additional metal selected from the group formed by the metals from groups IIIA, IVA and VIIB,
optionally a sulphur content which is preferably such that the ratio of the number of moles of sulphur to the number of moles of metal(s) from group VIII is in the range 0.3 to 3,
at least one matrix, preferably alumina, providing the complement to 100% in the catalyst.

The Isomerization Process

The present invention also concerns a process for the isomerization of a cut containing at least one aromatic compound containing eight carbon atoms per molecule, said process comprising bringing said aromatic cut into contact with at least said catalyst in accordance with the invention present in a catalytic reactor.

Said aromatic cut containing at least one aromatic compound containing eight carbon atoms per molecule in particular comprises, as the aromatic compound containing eight carbon atoms per molecule, either a mixture of solely xylenes or solely ethylbenzene, or a mixture of xylene(s) and ethylbenzene.

Said isomerization process is generally carried out under the following operating conditions:
- a temperature of 300° C. to 500° C., preferably 320° C. to 450° C. and highly preferably 340° C. to 430° C.;
- a partial pressure of hydrogen of 0.3 to 1.5 MPa, preferably 0.4 to 1.2 MPa and yet more preferably 0.7 to 1.2 MPa;
- a total pressure of 0.45 to 1.9 MPa, preferably 0.6 to 1.5 MPa; and
- a supply space velocity, expressed in kilograms of feed introduced per kilogram of catalyst and per hour, of 0.25 to 30 $h^{-1}$, preferably 1 to 10 $h^{-1}$ and more preferably 2 to 6 $h^{-1}$.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1657146, filed Jul. 26, 2016 are incorporated by reference herein.

The following examples illustrate the invention without, however, limiting the scope.

EXAMPLES

Example 1 (not in Accordance with the Invention): Preparation of Isomerization Catalyst a Catalyst A was a catalyst comprising an IZM-2 zeolite, platinum, and a matrix alumina. This IZM-2 zeolite was synthesised in accordance with the disclosure of patent FR 2 918 050 B. A colloidal suspension of silica known by the commercial name Ludox HS-40 marketed by Aldrich was incorporated into a solution composed of sodium hydroxide (Prolabo), 1,6-bis(methylpiperidinium)hexane dibromide template, aluminium hydroxide (Aldrich) and deionized water. The molar composition of the mixture was as follows: 1 $SiO_2$; 0.0033 $Al_2O_3$; 0.1666 $Na_2O$; 0.1666 1,6-bis(methylpiperidinium)hexane; 33.3333 $H_2O$. The mixture was stirred vigorously for half an hour. The mixture was then transferred, after homogenization, into a PARR type autoclave. The autoclave was heated for 5 days at 170° C. with rotating spindle stirring (30 rpm). The product obtained was filtered, washed with deionized water to obtain a neutral pH then oven dried overnight at 100° C. The solid was then introduced into a muffle furnace for calcining therein in order to eliminate the template. The calcining cycle comprised raising the temperature to 200° C., a constant temperature stage at this temperature for two hours, raising the temperature to 550° C. followed by an eight hour constant temperature stage at this temperature, and finally a return to ambient temperature. The temperature rises were carried out at a rate of 2° C./min. The solid thus obtained was then placed under reflux for 2 hours in an aqueous solution of ammonium nitrate (10 ml of solution per gram of solid, concentration of ammonium nitrate 3M) in order to exchange the alkaline sodium atoms for ammonium ions. This reflux step was carried out four times with a fresh solution of ammonium nitrate, then the solid was filtered, washed with deionized water and oven dried overnight at 100° C. Finally, in order to obtain the zeolite in its acid form (protonated, $H^+$), a calcining step was carried out at 550° C. for ten hours (temperature ramp-up 2° C./min) in flushed bed mode in dry air (2 normal liters per hour and per gram of solid). The solid thus obtained was analysed by X Ray Diffraction and identified as being constituted by IZM-2 zeolite. The zeolite, denoted IZM-2_A, was used to prepare the catalyst. Characterizations using $^{27}Al$ NMR, X ray fluorescence and ICP methods provided access to the following results for the IZM-2_A:
- percentage by weight of hexacoordinated aluminium atoms $Al^{VI}$: 9%,
- ratio of the number of moles of silicon divided by the number of moles of framework aluminium, in mole/mole, Si/Al: 113,
- ratio of the number of moles of sodium divided by the number of moles of framework aluminium, in mole/mole, Na/Al: 0.22.

Platinum was deposited onto a gamma alumina matrix using an excess impregnation method. The gamma alumina provided by Axens (GOD200) was in the form of beads. Firstly, the beads were saturated by filling the pore volume with distilled water (dropwise addition) then wetting, typically for 30 minutes. Next, the alumina was acidified with an aqueous solution of acid in an amount of 5% by weight of chlorine with respect to the mass of dry alumina (4 ml of solution per gram of solid) and stirring was continued for one hour on the stirring table, then the solution was removed. Next, excess impregnation was carried out with an aqueous solution of hexachloroplatinic acid with an amount of 2% by weight of platinum with respect to the mass of dry alumina (4 ml of solution per gram of solid), then stirring was continued on the stirring table for 24 hours, then the solution was removed and the solid was rinsed with twice the exchange volume of distilled water. The solid was then oven dried overnight at 110° C. and calcined in a flow of dry air in flushed bed mode (1 normal liter per hour and per gram of solid) under the following conditions:
- temperature ramp-up from ambient to 150° C. at 5° C./min,
- constant temperature stage for one hour at 150° C.,
- ramp-up from 150° C. to 250° C. at 5° C./min,
- constant temperature stage for one hour at 250° C.,
- ramp-up from 250° C. to 350° C. at 5° C./min,
- constant temperature stage for one hour at 350° C.,
- ramp-up from 350° C. to 520° C. at 5° C./min,
- constant temperature stage for two hours at 520° C.,
- drop to ambient temperature.

Characterizations by X ray fluorescence, Castaing microprobe and $H_2/O_2$ titration provided access to the following results for the solid:
- percentage of platinum (dry mass): 1.7%,
- dispersion of platinum: 82%,
- platinum distribution coefficient: 0.99.

Catalyst A was then prepared by combining the IZM-2 zeolite_A and the alumina impregnated with platinum as follows. Firstly, the granulometry of the starting powders was controlled by sieving the IZM-2_A and grinding-sieving alumina beads impregnated with platinum in order to obtain a granulometry which was advantageously below 63 microns for the two solids. After weighing out the desired masses of solids, the mechanical mixture (2 grams of dry mass) of the two powders was mixed with the aid of a bucket mill for 2 minutes, using a ball and a frequency of 30 Hz. The mixture was then pelletized at 4 metric tons with a Carver hydraulic press then ground and sieved to the preferred granulometry of 250-500 microns. Catalyst A had the following composition:

10% by weight of the IZM-2 zeolite_A,
1.5% by weight of platinum,
88.5% by weight of impregnated alumina.

Example 2 (in Accordance with the Invention): Preparation of Isomerization Catalyst B Catalyst B was a catalyst comprising an IZM-2 zeolite, platinum, and a matrix alumina. This IZM-2 zeolite was synthesised in accordance with the disclosure of patent FR 2 918 050 B. A colloidal suspension of silica known by the commercial name Ludox HS-40 marketed by Aldrich was incorporated into a solution composed of sodium hydroxide (Prolabo), 1,6-bis(methylpiperidinium)hexane dibromide template, aluminium hydroxide (Aldrich) and deionized water. The molar composition of the mixture was as follows: 1 $SiO_2$; 0.0045 $Al_2O_3$; 0.1666 $Na_2O$; 0.1666 1,6-bis(methylpiperidinium)hexane; 33.3333 $H_2O$. The mixture was stirred vigorously for half an hour. The mixture was then transferred, after homogenization, into a PARR type autoclave. The autoclave was heated for 5 days at 170° C. with rotating spindle stirring (30 rpm). The product obtained was filtered, washed with deionized water to obtain a neutral pH then oven dried overnight at 100° C. The solid was then introduced into a muffle furnace for calcining therein in order to eliminate the template. The calcining cycle comprised raising the temperature to 200° C., a constant temperature stage at this temperature for two hours, raising the temperature to 550° C. followed by an eight hour constant temperature stage at this temperature, and finally a return to ambient temperature. The temperature rises were carried out at a rate of 2° C./min. The solid thus obtained was then placed under reflux for 2 hours in an aqueous solution of ammonium nitrate (10 ml of solution per gram of solid, concentration of ammonium nitrate 3M) in order to exchange the alkaline sodium atoms for ammonium ions. This reflux step was carried out four times with a fresh solution of ammonium nitrate, then the solid was filtered, washed with deionized water and oven dried overnight at 100° C. Finally, in order to obtain the zeolite in its acid form (protonated, $H^+$), a calcining step was carried out at 550° C. for ten hours (temperature ramp-up 2° C./min) in flushed bed mode in dry air (2 normal liters per hour and per gram of solid). The solid thus obtained was analysed by X Ray Diffraction and identified as being constituted by IZM-2 zeolite. The zeolite, denoted IZM-2_B, was used to prepare the catalyst. Characterizations using $^{27}Al$ NMR, X ray fluorescence and ICP methods provided access to the following results for the IZM-2_B:

percentage by weight of hexacoordinated aluminium atoms $Al^{VI}$: 13%,
ratio of the number of moles of silicon divided by the number of moles of framework aluminium, in mole/mole, Si/Al: 91,
ratio of the number of moles of sodium divided by the number of moles of framework aluminium, in mole/mole, Na/Al: 0.28.

To prepare catalyst B, the sample of alumina impregnated with platinum prepared as described in Example 1 was used. Catalyst B was prepared by following the preparation protocol given for catalyst A in Example 1. Catalyst B had the following composition:

10% by weight of the IZM-2 zeolite_B,
1.5% by weight of platinum,
88.5% by weight of impregnated alumina.

Example 3 (in Accordance with the Invention): Preparation of Isomerization Catalyst C Catalyst C was a catalyst comprising an IZM-2 zeolite, platinum, and a matrix alumina. This IZM-2 zeolite was synthesised in accordance with the disclosure of patent FR 2 918 050 B. A colloidal suspension of silica known by the commercial name Ludox HS-40 marketed by Aldrich was incorporated into a solution composed of sodium hydroxide (Prolabo), 1,6-bis(methylpiperidinium)hexane dibromide template, aluminium hydroxide (Aldrich) and deionized water. The molar composition of the mixture was as follows: 1 $SiO_2$; 0.0055 $Al_2O_3$; 0.1666 $Na_2O$; 0.1666 1,6-bis(methylpiperidinium)hexane; 33.3333 $H_2O$. The mixture was stirred vigorously for half an hour. The mixture was then transferred, after homogenization, into a PARR type autoclave. The autoclave was heated for 5 days at 170° C. with rotating spindle stirring (30 rpm). The product obtained was filtered, washed with deionized water to obtain a neutral pH then oven dried overnight at 100° C. The solid was then introduced into a muffle furnace for calcining therein in order to eliminate the template. The calcining cycle comprised raising the temperature to 200° C., a constant temperature stage at this temperature for two hours, raising the temperature to 550° C. followed by an eight hour constant temperature stage at this temperature, and finally a return to ambient temperature. The temperature rises were carried out at a rate of 2° C./min. The solid thus obtained was then placed under reflux for 2 hours in an aqueous solution of ammonium nitrate (10 ml of solution per gram of solid, concentration of ammonium nitrate 3M) in order to exchange the alkaline sodium atoms for ammonium ions. This reflux step was carried out four times with a fresh solution of ammonium nitrate, then the solid was filtered, washed with deionized water and oven dried overnight at 100° C. Finally, in order to obtain the zeolite in its acid form (protonated, $H^+$), a calcining step was carried out at 550° C. for ten hours (temperature ramp-up 2° C./min) in flushed bed mode in dry air (2 normal liters per hour and per gram of solid). The solid thus obtained was analysed by X Ray Diffraction and identified as being constituted by IZM-2 zeolite. The zeolite, denoted IZM-2_C, was used to prepare the catalyst. Characterizations using $^{27}Al$ NMR, X ray fluorescence and ICP methods provided access to the following results for the IZM-2_C:

percentage by weight of hexacoordinated aluminium atoms $Al^{VI}$: 11%,
ratio of the number of moles of silicon divided by the number of moles of framework aluminium, in mole/mole, Si/Al: 78, ratio of the number of moles of sodium divided by the number of moles of framework aluminium, in mole/mole, Na/Al: 0.18.

To prepare catalyst C, the sample of alumina impregnated with platinum prepared as described in Example 1 was used. Catalyst C was prepared by following the preparation protocol given for catalyst A in Example 1. Catalyst C had the following composition:
- 10% by weight of the IZM-2 zeolite_C,
- 1.5% by weight of platinum,
- 88.5% by weight of impregnated alumina.

Example 4 (in Accordance with the Invention): Preparation of Isomerization Catalyst D Catalyst D was a catalyst comprising an IZM-2 zeolite, platinum, and a matrix alumina. This IZM-2 zeolite was synthesised in accordance with the disclosure of patent FR 2 918 050 B. A colloidal suspension of silica known by the commercial name Ludox HS-40 marketed by Aldrich was incorporated into a solution composed of sodium hydroxide (Prolabo), 1,6-bis(methylpiperidinium)hexane dibromide template, aluminium hydroxide (Aldrich) and deionized water. The molar composition of the mixture was as follows: 1 $SiO_2$; 0.0072 $Al_2O_3$; 0.1666 $Na_2O$; 0.1666 1,6-bis(methylpiperidinium)hexane; 33.3333 $H_2O$. The mixture was stirred vigorously for half an hour. The mixture was then transferred, after homogenization, into a PARR type autoclave. The autoclave was heated for 5 days at 170° C. with rotating spindle stirring (30 rpm). The product obtained was filtered, washed with deionized water to obtain a neutral pH then oven dried overnight at 100° C. The solid was then introduced into a muffle furnace for calcining therein in order to eliminate the template. The calcining cycle comprised raising the temperature to 200° C., a constant temperature stage at this temperature for two hours, raising the temperature to 550° C. followed by an eight hour constant temperature stage at this temperature, and finally a return to ambient temperature. The temperature rises were carried out at a rate of 2° C./min. The solid thus obtained was then placed under reflux for 2 hours in an aqueous solution of ammonium nitrate (10 ml of solution per gram of solid, concentration of ammonium nitrate 3M) in order to exchange the alkaline sodium atoms for ammonium ions. This reflux step was carried out four times with a fresh solution of ammonium nitrate, then the solid was filtered, washed with deionized water and oven dried overnight at 100° C. Finally, in order to obtain the zeolite in its acid form (protonated, $H^+$), a calcining step was carried out at 550° C. for ten hours (temperature ramp-up 2° C./min) in flushed bed mode in dry air (2 normal liters per hour and per gram of solid). The solid thus obtained was analysed by X Ray Diffraction and identified as being constituted by IZM-2 zeolite. The zeolite, denoted IZM-2_D, was used to prepare the catalyst. Characterizations using $^{27}Al$ NMR, X ray fluorescence and ICP methods provided access to the following results for the IZM-2_D:
- percentage by weight of hexacoordinated aluminium atoms $Al^{VI}$: 12%,
- ratio of the number of moles of silicon divided by the number of moles of framework aluminium, in mole/mole, Si/Al: 63,
- ratio of the number of moles of sodium divided by the number of moles of framework aluminium, in mole/mole, Na/Al: 0.19.

To prepare catalyst D, the sample of alumina impregnated with platinum prepared as described in Example 1 was used. Catalyst D was prepared by following the preparation protocol given for catalyst A in Example 1. Catalyst D had the following composition:
- 10% by weight of the IZM-2 zeolite_D,
- 1.5% by weight of platinum,
- 88.5% by weight of impregnated alumina.

Example 5 (not in Accordance with the Invention): Preparation of Isomerization Catalyst E Catalyst E was a catalyst comprising an IZM-2 zeolite, platinum, and a matrix alumina. This IZM-2 zeolite was synthesised in accordance with the disclosure of patent FR 2 918 050 B. A colloidal suspension of silica known by the commercial name Ludox HS-40 marketed by Aldrich was incorporated into a solution composed of sodium hydroxide (Prolabo), 1,6-bis(methylpiperidinium)hexane dibromide template, aluminium hydroxide (Aldrich) and deionized water. The molar composition of the mixture was as follows: 1 $SiO_2$; 0.0100 $Al_2O_3$; 0.1666 $Na_2O$; 0.1666 1,6-bis(methylpiperidinium)hexane; 33.3333 $H_2O$. The mixture was stirred vigorously for half an hour. The mixture was then transferred, after homogenization, into a PARR type autoclave. The autoclave was heated for 5 days at 170° C. with rotating spindle stirring (30 rpm). The product obtained was filtered, washed with deionized water to obtain a neutral pH then oven dried overnight at 100° C. The solid was then introduced into a muffle furnace for calcining therein in order to eliminate the template. The calcining cycle comprised raising the temperature to 200° C., a constant temperature stage at this temperature for two hours, raising the temperature to 550° C. followed by an eight hour constant temperature stage at this temperature, and finally a return to ambient temperature. The temperature rises were carried out at a rate of 2° C./min. The solid thus obtained was then placed under reflux for 2 hours in an aqueous solution of ammonium nitrate (10 ml of solution per gram of solid, concentration of ammonium nitrate 3M) in order to exchange the alkaline sodium atoms for ammonium ions. This reflux step was carried out four times with a fresh solution of ammonium nitrate, then the solid was filtered, washed with deionized water and oven dried overnight at 100° C. Finally, in order to obtain the zeolite in its acid form (protonated, $H^+$), a calcining step was carried out at 550° C. for ten hours (temperature ramp-up 2° C./min) in flushed bed mode in dry air (2 normal liters per hour and per gram of solid). The solid thus obtained was analysed by X Ray Diffraction and identified as being constituted by IZM-2 zeolite. The zeolite, denoted IZM-2_E, was used to prepare the catalyst. Characterizations using $^{27}Al$ NMR, X ray fluorescence and ICP methods provided access to the following results for the IZM-2_E:
- percentage by weight of hexacoordinated aluminium atoms $Al^{VI}$: 6%,
- ratio of the number of moles of silicon divided by the number of moles of framework aluminium, in mole/mole, Si/Al: 46,
- ratio of the number of moles of sodium divided by the number of moles of framework aluminium, in mole/mole, Na/Al: 0.08.

To prepare catalyst E, the sample of alumina impregnated with platinum prepared as described in Example 1 was used. Catalyst E was prepared by following the preparation protocol given for catalyst A in Example 1. Catalyst E had the following composition:
- 10% by weight of the IZM-2 zeolite_E,
- 1.5% by weight of platinum,
- 88.5% by weight of impregnated alumina.

Example 6: Evaluation of Catalytic Properties of Catalysts a, B, C, D, E, in the Isomerization of a $C_8$ Aromatics Cut The catalysts were tested in the isomerization of a $C_8$ aromatics cut composed by ethylbenzene (19% by weight), ortho-xylene (16% by weight), meta-xylene (58% by weight) and ethylcyclohexane (7% by weight). The tests were carried out in a micro-unit using a fixed bed reactor operating in downflow mode without recycle. The hydrocarbon effluents were analysed online by gas phase chromatography. Before being charged into the unit, the catalyst was first oven dried at least overnight at 110° C. Once charged into the unit, the catalyst underwent a first drying step under nitrogen under the following conditions:
  flow rate of nitrogen: 5 normal liters per hour and per gram of catalyst,
  total pressure: 1.3 MPa,
  temperature ramp-up from ambient temperature to 150° C.: 10° C./min,
  constant temperature stage at 150° C. for 30 minutes.

After drying, the nitrogen was replaced with hydrogen and a step for reduction in a flow of pure hydrogen was then carried out under the following conditions:
  flow rate of nitrogen: 4 normal liters per hour and per gram of catalyst,
  total pressure: 1.3 MPa,
  temperature ramp-up from 150° C. to 480° C.: 5° C./min,
  constant temperature stage at 480° C. for 2 hours.

The temperature was then dropped to 425° C. and the catalyst was stabilized for 24 hours in a stream of hydrogen and hydrocarbons (mixture of 20% by weight of ethylbenzene and 80% by weight of ortho-xylene), under the following operating conditions:
  supply space velocity of 5 grams of hydrocarbon per hour and per gram of catalyst,
  molar ratio of hydrogen to hydrocarbons of 4,
  total pressure of 1.3 MPa.

After the stabilization step, the temperature was then dropped to 385° C. and the catalyst was brought into contact with the $C_8$ aromatics cut mentioned above under the following conditions:
  supply space velocity of 3.5 grams of $C_8$ aromatics cut per hour and per gram of catalyst,
  molar ratio of hydrogen to hydrocarbons of 4,
  total pressure of 0.86 MPa.

The catalyst was kept under these operating conditions for 7 hours, then the catalytic performances were evaluated, employing the various operating conditions which are recorded in Table 2 below. The variation in the supply space velocity meant that the degrees of conversion into ethylbenzene and of isomerization of the xylenes, and thus the production of para-xylene, could be varied. For each operating condition, two analyses by chromatography were carried out in order to measure the performances of the catalysts.

TABLE 2

Operating conditions employed for catalytic evaluation

| Conditions | 1 | 2 | 3 | 4 | 5 | 6 |
|---|---|---|---|---|---|---|
| Duration of each condition (h) | 2.8 | 2.1 | 2.1 | 2.1 | 2.1 | 2.1 |
| Temperature (° C.) | 385 | 385 | 385 | 385 | 385 | 385 |
| Supply space velocity ($h^{-1}$) | 3.5 | 4.5 | 6.0 | 9.0 | 12.0 | 20.0 |
| $H_2$/hydrocarbons (mole/mole) | 4 | 4 | 4 | 4 | 4 | 4 |
| Total pressure (MPa) | 0.86 | 0.86 | 0.86 | 0.86 | 0.86 | 0.86 |

The para-xylene (PX) yield in the hydrocarbon effluent obtained at a supply space velocity of 20 $h^{-1}$ was used to evaluate the activity of the catalysts for the production of para-xylene:
PX=% by weight of para-xylene in the hydrocarbon effluent, where PX is the yield of para-xylene as a % by weight.
The change in the net losses yield (PN) as a function of the yield of para-xylene could itself be used to evaluate the selectivity of the catalyst. All hydrocarbon molecules apart from the cyclic molecules containing eight carbon atoms are considered to be net losses:

PN=100-PX-EB-OX-MX-N8 where:
PN: net losses yield in the hydrocarbon effluent, as a % by weight,
PX: % by weight of para-xylene in the hydrocarbon effluent,
EB: % by weight of ethylbenzene in the hydrocarbon effluent,
OX: % by weight of ortho-xylene in the hydrocarbon effluent,
MX: % by weight of meta-xylene in the hydrocarbon effluent,
N8: % by weight of naphthenes containing eight carbon atoms in the hydrocarbon effluent.

Table 3 thus reports the yield of para-xylene for catalysts A, B, C, D and E at a space velocity of 20 $h^{-1}$ as well as the net losses estimated for a yield of para-xylene of 18% for the catalysts. The net losses (PN) at 18% of the para-xylene yield were estimated by linear extrapolation or interpolation of the experimental data for the change in net losses yield as a function of the para-xylene yield. Catalysts A, B, C, D and E are only distinguished by the nature of the IZM-2 zeolite forming part of their composition.

Catalyst E, which employed the IZM-2_E with a Si/Al ratio of 46, was the most active catalyst of the series of catalysts but, in contrast, it was far less selective than the other catalysts. Catalyst A, which employed the IZM-2_A with a Si/Al ratio of 113, was the least active solid of the series of catalysts, although its selectivity remained comparable to those of catalysts B, C, D. In summary, using the zeolites IZM-2_B (Si/Al of 91), C (Si/Al of 78) and D (Si/Al of 63) meant that a better activity than with the IZM-2 zeolite_A (Si/Al of 113) and a better selectivity than with the IZM-2 zeolite_E (Si/Al of 46) was obtained.

TABLE 3

Catalytic performances of catalysts A, B, C, D and E

| Catalyst | A | B | C | D | E |
|---|---|---|---|---|---|
| Molar ratio, Si/Al (IZM-2) | 113 | 91 | 78 | 63 | 46 |
| Para-xylene yield at space velocity of 20 $h^{-1}$ | 7.6 | 12.6 | 14.7 | 16.6 | 17.7 |

TABLE 3-continued

Catalytic performances of catalysts A, B, C, D and E

| Catalyst | A | B | C | D | E |
|---|---|---|---|---|---|
| Net losses yield at a para-xylene yield of 18% | 2.5 | 2.8 | 2.6 | 2.8 | 3.8 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the isomerization of a cut containing at least one aromatic compound containing eight carbon atoms per molecule, said process comprising bring said cut into contact with at least one catalyst comprising at least one IZM-2 zeolite, at least one matrix and at least one metal from group VIII of the periodic classification of the elements, said catalyst having a ratio between the number of moles of silicon and the number of moles of aluminum of the IZM 2 zeolite of 60 to 95, said process being carried out under the following operating conditions:
   a temperature of 340° C. to 430° C.,
   a partial pressure of hydrogen of 0.4 to 1.2 MPa,
   a total pressure of 0.45 to 1.9 MPa, and
   a supply space velocity, expressed in kilograms of feed introduced per kilogram of catalyst and per hour, of 0.25 to 30 $h^{-1}$.

2. The process as claimed in claim 1, in which the ratio between the number of moles of silicon and the number of moles of aluminum for the IZM-2 zeolite of the catalyst employed is in the range 70 to 95.

3. The process as claimed in claim 1, in which the ratio between the number of moles of silicon and the number of moles of aluminum for the IZM-2 zeolite of the catalyst employed is in the range to 80 to 95.

4. The process as claimed in claim 1, in which the IZM-2 zeolite of the catalyst employed is in the acid form.

5. The process as claimed in claim 1, in which said matrix employed is alumina, silica, silica-alumina, a clay, titanium oxide, boron oxide or zirconia, used alone or as a mixture, or an aluminate.

6. The process as claimed in claim 5, in which the catalyst matrix employed is alumina.

7. The process as claimed in claim 1, in which the metal from group VIII of the catalyst employed is iron, cobalt, nickel, ruthenium, rhodium, palladium, osmium, iridium or platinum.

8. The process as claimed in claim 1, in which the catalyst employed additionally comprises at least one metal from groups IIIA, IVA or VIM of the periodic classification of the elements.

9. The process as claimed in claim 1, in which the catalyst employed further comprises sulfur.

10. The process as claimed in claim 1, in which the catalyst employed comprises:
    1% to 90% of the IZM-2 zeolite,
    0.01% to 4% of at least one metal from group VIII of the periodic classification of the elements,
    optionally 0.01% to 2% of at least one additional metal from groups IIIA, IVA or VIIB,
    optionally a sulfur content such that the ratio of the number of moles of sulfur to the number of moles of metal(s) from group VIII is in the range 0.3 to 3,
    at least one matrix providing the complement to 100% in the catalyst.

11. The isomerization process as claimed in claim 1, in which said aromatic cut containing at least one aromatic compound containing eight carbon atoms per molecule comprises, as the aromatic compound containing eight carbon atoms per molecule, either solely a mixture of xylenes, or solely ethylbenzene, or a mixture of xylene(s) and ethylbenzene.

12. The process as claimed in claim 1, in which the metal from group VIII of the catalyst employed is platinum or palladium.

13. The process as claimed in claim 1, in which the metal from group VIII of the catalyst employed is platinum.

14. The process as claimed in claim 1, in which the catalyst employed additionally comprises gallium, tin, indium, or rhenium.

* * * * *